United States Patent [19]

Mueller, Jr.

[11] Patent Number: 4,632,670
[45] Date of Patent: Dec. 30, 1986

[54] SUTURE TAB

[75] Inventor: Richard L. Mueller, Jr., Athens, Tex.
[73] Assignee: Argon Medical Corp., Athens, Tex.
[21] Appl. No.: 719,850
[22] Filed: Apr. 4, 1985
[51] Int. Cl.⁴ .............................................. A61M 5/00
[52] U.S. Cl. .............................. 604/174; 128/DIG. 26
[58] Field of Search ................................ 604/174–180; 128/DIG. 26, 133

[56] References Cited

U.S. PATENT DOCUMENTS

| | | | |
|---|---|---|---|
| 3,568,679 | 3/1971 | Reif | 604/180 X |
| 3,630,195 | 12/1971 | Santomieri | 604/180 X |
| 4,276,882 | 7/1981 | Diekhudt | 128/DIG. 26 X |
| 4,435,174 | 3/1984 | Redmond et al. | 604/174 |

Primary Examiner—Stephen C. Pellegrino
Attorney, Agent, or Firm—Lawrence S. Levinson; Sanford J. Asman

[57] ABSTRACT

A suture tab for holding a catheter in place on a patient is described. The suture tab includes a central opening adapted to receive and hold a catheter in place. A slit extends from one edge of the suture tab to the central opening such that the catheter must pass through the slit to arrive at the central opening. A suture placed through the suture tab serves to both close the slit and hold the suture tab in place on the patient.

2 Claims, 4 Drawing Figures

U.S. Patent    Dec. 30, 1986    4,632,670
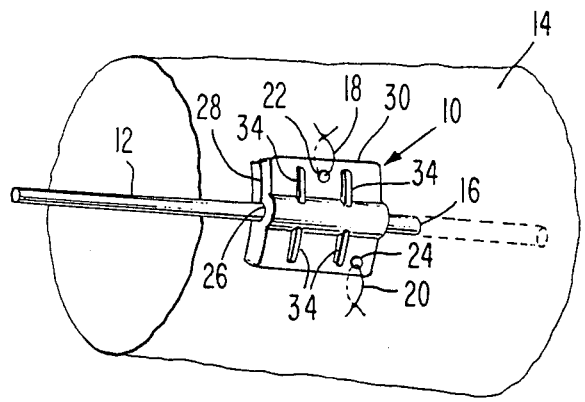
*Fig_1_*
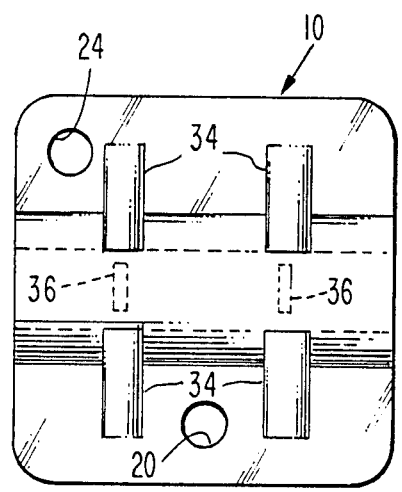
*Fig_2_*
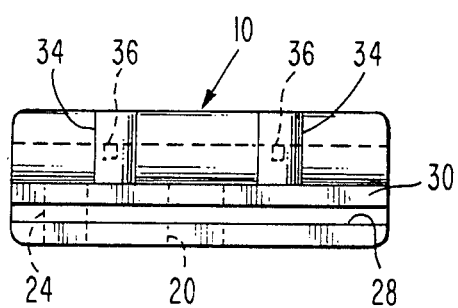
*Fig_3_*
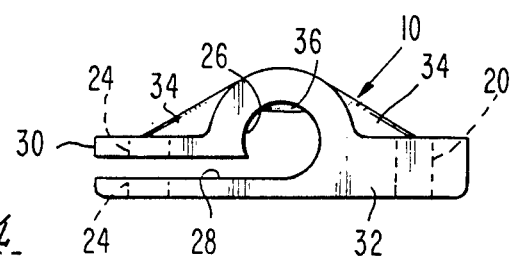
*Fig_4_*

SUTURE TAB

BACKGROUND OF THE INVENTION

The present invention relates to a device for holding a catheter in place. In particular, it relates to an improved suture tab.

In many medical procedures, catheters are used. A catheter is a tube which extends into a lumen of a patient. In order to prevent catheters from moving around where they exit from a patient's lumen, they are often taped into place. For example, a catheter entering a patient's vein through either a cutdown or by using the Seldinger technique (in which a needle is placed into the patient, followed by a guide wire placed through the needle which is then slid back over the guide wire and replace by sliding the catheter down over the guide wire) in the patient's arm will often be taped in place on the patient. Rather than taping the catheter in place, rubber or plastic devices, called suture tabs which have an opening for a catheter may be used.

A suture tab typically encloses a good portion of a catheter and is then sutured in place with a number of sutures to the arm of the patient where it keeps the catheter stationary. In one suture tab of the prior art, the cross-section of the suture tab is substantially horseshoe-like, i.e., it is shaped like the Greek letter omega (Ω). Such a suture tab is typically placed over the catheter via the opening at the bottom and then a loop is placed around a portion of the suture tab which is then sutured on either side to the patient's arm. Thus, the application of this suture tab around the catheter and securing it to the patient's arm requires a minimum of three steps, i.e., a suture around the tab to hold it closed on the the catheter followed by the two sutures to the patient's arm.

In view of the desirability to reduce the number of steps required to apply a suture tab and hold it in place, an improved suture tab would be desirable.

SUMMARY OF THE INVENTION

The suture tab of the present invention is constructed to have a wrap-around cross-section such that it is applied over a catheter and then sutured in place with a single suture which effectively locks the suture tab in place on the catheter as well as attaching it to the patient's arm. If desired, a second suture may be used.

BRIEF DESCRIPTION OF THE DRAWINGS

In the Drawing:

FIG. 1 shows the suture tab of the present invention applied to a patient's arm holding a catheter in place;

FIG. 2 is a top view of the suture tab of the present invention;

FIG. 3 is a front view of the suture tab of the present invention; and

FIG. 4 is a side view of the suture tab of the present invention.

DETAILED DESCRIPTION OF THE PREFERRED EMBODIMENT

Referring to FIG. 1, the suture tab 10 of the present invention is shown applied to a catheter 12 which enters the arm 14 of a patient at a location 16. The suture tab 10 is sutured to the patient's arm 14 using sutures 18, 20 which pass through openings 22, 24, respectively, in the suture tab 10.

Referring now to FIGS. 1-4, the suture tab 10 is comprised of a molded, flexible piece of plastic or rubber, such as polyvinyl chloride (PVC), a soft urethane, or silicone, having a central opening 26, as shown in cross-section in FIG. 4, which has an inside diameter adapted to receive a catheter (see FIG. 1). On one side of the central opening 26, there is a slit 28 which extends out through one end 30 of the suture tab 10. The other side 32 of the suture tab 10 surrounds the central opening 26. Stiffening gussets 34 serve to preserve the shape of the suture tab 10. Thus, when the slit 28 is separated to surround a catheter 12, the stiffening gussets 34 serve to help close the slit 28 around the catheter 12.

The material of which the suture tab 10 is constructed is selected to have suitable flexibility such that it can be readily opened around a catheter and placed in position on a patient. In addition, the material is preferably selected to provide a high coefficient of friction in order to prevent the catheter 12 from sliding longitudinally through the opening 26 after the suture tab 10 has been placed on a patient. Optionally, ribs 36 may be included within the central opening 26 for the purpose of securely holding the catheter 12 in place. If used, the ribs 36 may have a crescent shape, as shown in FIG. 4. Two such ribs 36 are used in the embodiment shown in FIGS. 2-4.

In order to use the suture tab 10 of the present invention, the catheter 12 is first placed through a suitable cut down 16 into a lumen of the patient. Thereafter, the slit 28 is held open and the suture tab 10 is slid over the catheter 12, such that the catheter 12 is positioned within the central opening 26 of the suture tab 10. Thereafter, a first suture 18 is placed through the opening 20 to hold the slit 28 closed around the catheter 12. The suture 18 also serves to hold the suture tab 10 in place on the patient's arm 14. A second suture 20 may optionally be used to further hold the suture tab 10 in place. However, the use of the second suture 20 through the opening 24 does not serve to hold the slit 28 closed around the catheter 12.

As will be obvious to those of ordinary skill in the art, the use of a suture tab having a shape such that there is a slit through which a catheter must pass in order to arrive at a central opening having a shape adapted to receive the catheter means that a single suture can be used to both close the suture tab around the catheter and hold the suture tab in place on the patient. Accordingly, a critical feature of the present invention is the slit opening which extends into the central opening adapted to receive the catheter such that a single suture can both close the slit and hold the suture tab in place on the patient.

I claim:

1. An improved suture tab of the type which includes a central opening which surrounds a catheter that has been inserted into a patient and holds the catheter in place along the body of said patient by means of a suture which passes through both said suture tab and said patient, wherein the improvement comprises:

(a) said suture tab being made of plastic and having a base which is substantially rectangular in shape when viewed from above, said central opening extending from a connecting edge of said suture tab, tunnel-like through to an opposing edge of said suture tab;

(b) a slit which extends from said central opening out through said connecting edge of said suture tab base, said slit extending between said one edge of said suture tab and said opposing edge of said suture tab, whereby there is a layer of flexible material, when viewed from above, which extends between said central opening and said connecting edge and overlies said base, said layer of flexible material being capable of lifting to receive a catheter within said central opening, a pair of substantially aligned openings in the material on either side of said slit, whereby a single suture serves to simultaneously close said slit, thereby securing said suture tab to said catheter, to hold said suture tab in place on said patient, and to hold said catheter along the body of said patient;

(c) an opening which extends through said layer of flexible material and the portion of said base which extends between said central opening and said connecting edge; and (d) at least one stiffening gusset which extends above said slit from said layer of flexible material to the material on the outside of said central opening, said at least one stiffening gusset serving to help keep said central opening closed.

2. The improved suture tab of claim 1 further comprising at least one rib within said central opening, said at least one rib extending transversely to said central opening, wherein when said central opening is closed around a catheter said rib will apply holding pressure to keep said catheter in place.

* * * * *